(12) United States Patent
Sun et al.

(10) Patent No.: US 7,838,293 B2
(45) Date of Patent: Nov. 23, 2010

(54) **GENE *CRY7BA1* ENCODING AN INSECTICIDAL CRYSTAL PROTEIN OF *BACILLUS THURINGIENSIS***

(75) Inventors: Ming Sun, Hubei (CN); Ziniu Yu, Hubei (CN); Shouwen Chen, Hubei (CN); Zhenyu Zhang, Hubei (CN); Lifang Ruan, Hubei (CN); Suxia Guo, Hubei (CN); Jingyuan Dai, Hubei (CN); Lin Li, Hubei (CN); Ziduo Liu, Hubei (CN)

(73) Assignee: Huazhong Agricultural University, Wuhan (CN)

( * ) Notice: Subject to any disclaimer, the term of this patent is extended or adjusted under 35 U.S.C. 154(b) by 255 days.

(21) Appl. No.: 12/089,992

(22) PCT Filed: Oct. 17, 2006

(86) PCT No.: PCT/CN2006/002724

§ 371 (c)(1),
(2), (4) Date: Apr. 11, 2008

(87) PCT Pub. No.: WO2007/045160

PCT Pub. Date: Apr. 26, 2007

(65) Prior Publication Data

US 2009/0130758 A1    May 21, 2009

(30) Foreign Application Priority Data

Oct. 17, 2005    (CN) .................... 2005 1 0019596

(51) Int. Cl.
*C12N 15/32* (2006.01)
*C12N 15/82* (2006.01)
*C12N 1/00* (2006.01)
*C07K 14/325* (2006.01)

(52) U.S. Cl. .................... 435/419; 536/23.71; 530/350; 424/93.2

(58) Field of Classification Search .................... None
See application file for complete search history.

(56) References Cited

U.S. PATENT DOCUMENTS

2008/0070829 A1 *    3/2008    Carozzi et al. .................. 514/2

FOREIGN PATENT DOCUMENTS

| CN | 12-60397 A | | 7/2006 |
|---|---|---|---|
| WO | WO 93/08693 | * | 5/1993 |
| WO | WO 95/06730 A | | 3/1995 |

OTHER PUBLICATIONS

Dai et al (1996, Lett. Appl. Microbiol. 22:42-45).*
Crickmore et al (1998, Microbiol. Mol. Biol. Rev. 807-813).*
Sun Ming, et al.; "Characterization of the Insecticidal Crystal Protein Genes of *Bacillus thuringiensis* YBT-1520", *Acta Microbiologica Sinica* 40(4):365-371 (2000).

* cited by examiner

*Primary Examiner*—Anne Kubelik
(74) *Attorney, Agent, or Firm*—Scully, Scott, Murphy & Presser, P.C.

(57) ABSTRACT

The present invention discloses the isolation, cloning and use of insecticidal crystal proteins from *Bacillus thuringiensis*. The present invention isolates a novel insecticidal crystal protein gene cry7Ba1 from *B. thuringiensis* subsp. *huazhongensis* YBT-978 strain, and said gene encodes a novel insecticidal crystal protein Cry7Ba1, which shows insecticidal activity against Lepidopteran insects. The present invention also discloses the gene sequence of the novel insecticidal crystal protein, uses suitable expression vectors to transform micro-organisms so as to express the product Cry7Ba1 encoded by the gene and make it exert the insecticidal activity of the protein against Lepidopteran pests.

9 Claims, 4 Drawing Sheets

＃ GENE *CRY7BA1* ENCODING AN INSECTICIDAL CRYSTAL PROTEIN OF *BACILLUS THURINGIENSIS*

FIELD OF THE INVENTION

The present invention relates to micro-organism genetic engineering. In particular, the present invention relates to the separation and cloning of insecticidal crystal proteins from *Bacillus thuringiensis*. The present invention relates to the genetic engineering of biological pesticides.

BACKGROUND OF THE INVENTION

The *Bacillus thuringiensis* is a rod-shaped, Gram-positive, endospore-forming bacterium which is widely existing in various ecological environments. During the spore-forming phase, *B, thuringiensis* forms parasporal crystals consisting of Insecticidal Crystal Proteins (ICPs) which have specific toxicity against insects and specific biological activities to more than 500 species of insects in 10 orders belonging to the class Insecta, including Lepidoptera, Diptera, Coleoptera, Hymenoptera, Homoptera, etc, as well as to some harmful varieties in Protozoa, Nematomorpha, Platyhelminthes (Schnepf, H E., Crickmore, N., Rie, J. V., Lereclus, D., Baum, J., Feitelson, J., Zeigler, D. R. & Dean, D. H. 1998. *Bacillus thuringiensis* and its pesticidal crystal proteins. *Microbiol Mol Biol Rev* 62, 775-806).

Wildtype strains of *B. thuringiensis* typically have genes encoding insecticidal crystal proteins and each strain usually has multiple copies of said genes. Schnepf et al. cloned the first gene encoding insecticidal crystal protein in 1981 from *B. thuringiensis* subsp. *kurstaki* Strain HD1 and deduced the amino acid sequence of the first *B. thuringiensis* insecticidal crystal protein based on the DNA base sequence (Schnepf H E, Wong H C, Whiteley H R. The amino acid sequence of a crystal protein from *Bacillus thuringiensis* deduced from the DNA base sequence. *J Biol. Chem.* 1985 May 25; 260(10): 6264-6272.). Afterwards, new genes encoding insecticidal crystal proteins have been actively pursued in connection with studies of *B. thuringiensis*. Many new genes encoding different insecticidal crystal proteins have been identified, cloned and sequenced. Therefore, in 1995, the *B. thuringiensis* Pesticidal Crystal Protein Nomenclature Committee was founded by scholars including Crickmore in the Annual Meeting of the Society for Invertebrate Pathology. In 1996, a new classification system for the *B. thuringiensis* insecticidal crystal proteins based on the homology of amino acid sequences was formally proposed, and nomenclature rules and the principle for classification were set, wherein it stipulates that: cry gene is an insecticidal gene from *B. thuringiensis* encoding parasporal crystal protein, or any gene that has obvious sequence similarity to a known cry gene; cyt gene is a gene encoding a parasporal crystal protein from *B. thuringiensis* that exhibits hemolytic activity, or any gene encoding a protein that has obvious sequence similarity to a known Cyt protein. They are classified in 4 ranks based on the homology of the amino acid sequence deduced from the full length gene. The boundaries between each rank represent approximately 95%, 78% and 45% sequence identity. The genes of the insecticidal crystal protein are classified into 4 ranks. By August, 2005, the number of genes of *Bacillus thuringiensis* insecticidal crystal proteins has reached 319, representing varieties from 48 types (Crickmore, N., D. R. Zeigler, J. Feitelson, E. Schnepf, J. Van Rie, D. Lereclus, J. Baum, and D. H. Dean. 1998. Revision of the nomenclature for the *Bacillus thuringiensis* pesticidal crystal proteins. Microbiol. Mol. Biol. Rev. 62:807-813; see for example the internet site at lifesci.sussex.ac.uk/home/Neil_Crickmore/Bt/index.html on the world wide web).

In the beginning, pesticides based on *B. thuringiensis* are produced with screened wildtype strains. With the advancement of molecular biology, people have gradually altered the wildtype strains by genetic engineering means. At the same time, people have been keeping on transforming genes of *B. thuringiensis* insecticidal crystal proteins into plants and have been producing transgenic plants that are resistant to agricultural pests.

However, with the development of B.t. pesticides and the increasing usage of these pesticides, resistance in targeted pests has been continuously discovered by the scientists. The scholars have extensively studied the resistance against B.t pesticides in targeted pests. *Bacillus thuringiensis* insecticidal crystal proteins have to go through the following process in order to give the insecticidal effects: the solubilization of the crystals and activation of the protoxin crystals, binding of the toxin fragments to receptors on the epithelial linings in the midgut, and the insertion into the membrane to create pores, wherein the activity spectrum and toxicity mainly depend on the recognition and interaction of the toxin fragments with the specific receptors on the epithelial linings in the midgut of the insects. Further, the development of resistance against B.t. pesticides in insects is closely related to the recognition and binding to the pesticide receptor. Therefore, cloning and application of new, especially novel genes of insecticidal crystal proteins have become the key to prevent and control the resistance against B.t pesticides in targeted pests and the core issue in the various insect control strategies. In recent years, searching and cloning novel genes of insecticidal crystal proteins have been the most active area in the study for *B. thuringiensis*. The significance of the present invention lies in this. In China, a new subspecies, YBT-978 strain, which is a subspecies of *B. thuringiensis* has been separated and characterized in 1996, which belongs to subspecies *huazhongensis*, serotype H40 (for the source of the strain, please refer to Dai J et al. 1996. *Bacillus thuringiensis* subsp. *huazhongensis*, serotype H40, isolated from soils in the People's Republic of China. Letters in Applied Microbiology. 22(1): 42-45). It is found the parasporal crystal proteins has a highly efficient insecticidal activity to insects including *Plutella xylostella* through extracting said parasporal crystal proteins and subjecting to bioassays.

CONTENTS OF THE INVENTION

The object of the present invention is to isolate and clone the genes of insecticidal crystal proteins having high toxic potency from *B. thuringiensis* and to provide a use for the same.

Figure 1:
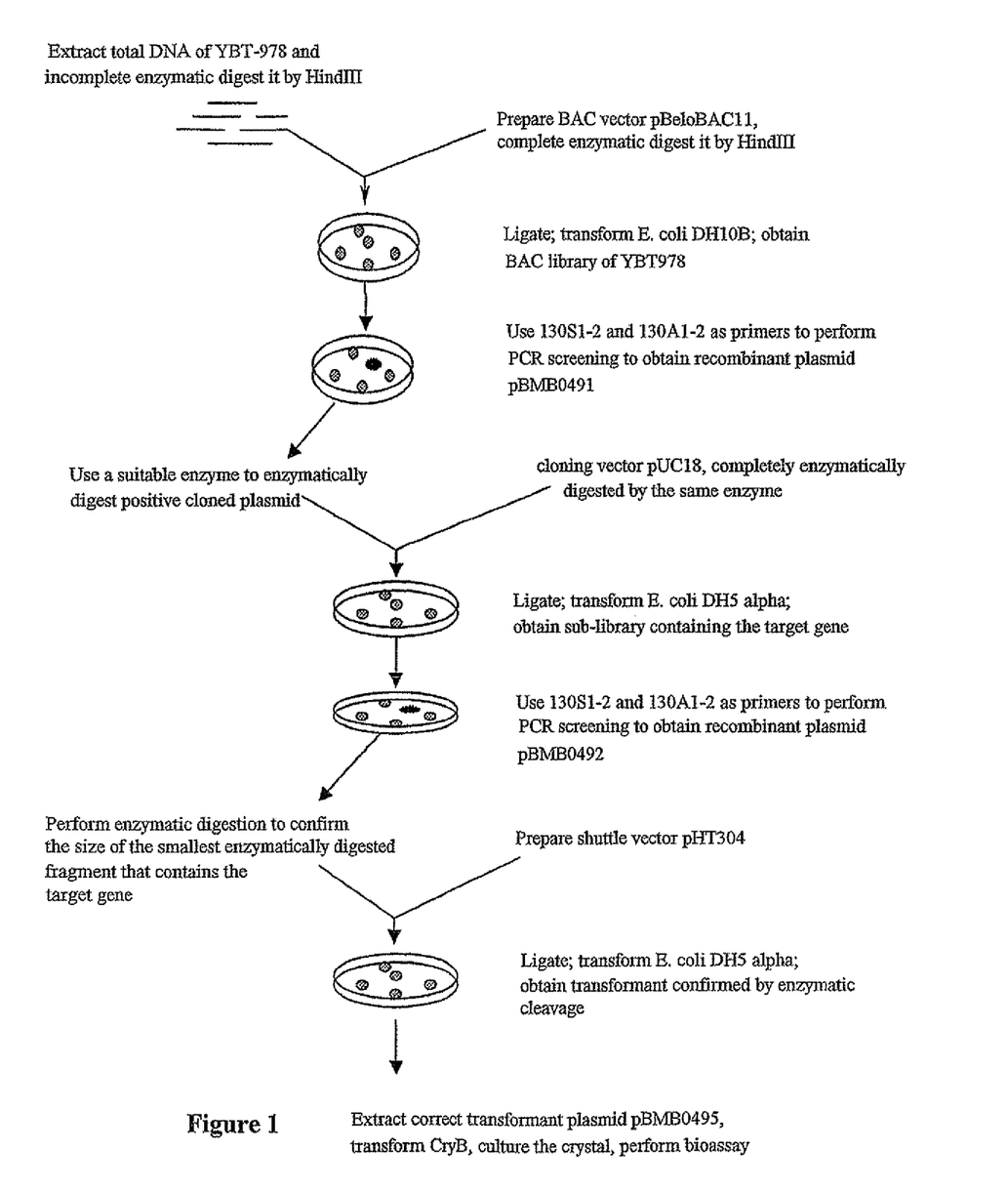
FIG. 1: Technical flowchart of the present invention

The technical scheme of the present invention is as shown in FIG. 1.

In order to achieve the aforesaid object, the present invention isolates from *Bacillus thuringiensis* subsp. *huazhongensis*, serotype H40, strain YBT-978 (for the source of the strain, please refer to Dai J et al. 1996. *Bacillus thuringiensis* subsp. *huazhongensis*, serotype H40, isolated from soils in the People's Republic of China. Letters in Applied Microbiology. 22(1): 42-45) a novel insecticidal crystal protein gene, the coding region of which consists of 3465 bases and has a nucleotide sequence shown in SEQ ID NO: 1. The cry7Ba1 gene of the present invention encodes Cry7Ba1 protein, which consists of 1154 amino acid residues and has an amino acid sequence as shown in SEQ ID NO:2. The gene cry7Ba1 of the present invention is expressed in microorganisms as Cry7Ba1 protein, which possesses insecticidal activity against insects of the order Lepidoptera.

The highest homology between the Cry7Ba1 protein of the present invention and any one of the proteins which has been disclosed is 58.2%. Moreover, the highest homology between the sequence of the N-terminal half of the Cry7Ba1 protein of the present invention (amino acid 1 to 658 of the amino acid sequence shown in SEQ ID NO:2) and any one of the proteins that has been disclosed is 37.1%.

The present invention provides the aforesaid gene sequence, which is a novel insecticidal crystal protein gene having insecticidal activity. The said gene can be used in transforming microorganisms and/or plants to impart insecticidal activity against pests of the Lepidoptera, as well as to overcome and delay the resistance in pests against genetically engineered insecticides and transgenic plants.

The following descriptions and examples disclose the technical solution in more detail:

It should be noted that the standard procedures and the reagents used on DNA are according to "Guide for Molecular Cloning Experiments" (refer to J. Sambrook et al (2002). Molecular Cloning: A Laboratory Manuel 3rd Edition. Translated by Jin Dong-yan et al. Science Press. Beijing).

1. The Sequencing of the N-Terminal Amino Acids of Crystal Protein Cry7Ba1 in *B. thuringiensis* YBT-978

The present invention uses *B. thuringiensis* YBT-978 as source strain for insecticidal crystal protein Cry7Ba1. *B. thuringiensis* YBT-978 is a standard strain of *B. thuringiensis* serotype H40, the source of which was recited in Dai J et al. 1996. The strain can form the typical rhombus-shaped crystals, and the molecular weight of the main component of the crystal protein Cry7Ba1 is about 130 kDa. The specific steps for sequencing the N-terminal amino acid sequence of Cry7Ba1 are as follows:

(1) The Culture of Bacterial Strains and the Manipulation of Culture

*B. thuringiensis* YBT-978 is inoculated on 5 ml LB (1% NaCl 1% peptone, 0.5% yeast extraction, pH 7.0) using an inoculation loop under sterile conditions and is incubated overnight in 30° C. on a shaker at 200 rpm. Then, 350 μl of the culture is transferred under sterile conditions to 35 ml ICPM culture medium (0.6% peptone, 0.5% glucose, 0.1% $CaCO_3$, 0.1% $MgSO_4.7H_2O$, 0.05% $KH_2PO_4$, pH 7.0), and is incubated in 30° C. on a shaker at 200 rpm until gemma and parasporal crystals completely fall off. The culture is collected and is centrifuged for 1 minute at 8000 rpm. Discard the supernatant. Use 0.5% NaCl solution and sterilized deionized water to rinse the precipitates for 3 times separately.

(2) The SDS-PAGE Electrophoresis of Crystal Proteins and the Transfer of PVDF Blotting Membrane Resuspend the rinsed precipitates in de-ionized water at a ratio of precipitates:de-ionized water=1:5 v/v, and add in an equal volume of 2× loading buffer. Mix, and then incubate in a boiling bath for 3 to 5 minutes, centrifuge at 12000 rpm for 5 minutes, and perform SDS-PAGE electrophoresis on the supernatant. For the formulation of 2× loading buffer and the procedure for performing SDS-PAGE electrophoresis, please refer to the method recited by Laemmli (Laemmli, UK. 1970. Digestion of structural proteins during the assembly of the head of bacteriophage T4. *Nature* (London) 227:680-685).

Then, the protein samples on the gel are transferred to PVDF membrane using Trans-Blot SD Semi-Dry Transfer Cell (BIO-RAD) using standard method (see Cook R G. 1994. Amino acid sequence analysis of blotted proteins, p. 207-220. In B. S. DunBar (ed.), Protein Blotting: A practical approach. Oxford University Press, New York).

(3) Determination of the N-Terminal Amino Acid Sequence of the Crystal Protein

Use a protein N-terminal amino acid sequencer (model number: ABI 491 Protein Sequence, ABI Procise) to sequence the N-terminal amino acid sequence. The sequencing result is N-terminal-MDIRNQNKYEVVYPA-C-terminal (SEQ ID NO: 3).

2. Acquisition of the sequence of 5' end DNA fragment of the insecticidal crystal protein gene cry7Ba1

Perform amplification using adaptor-ligation PCR. The principles and steps of adaptor-ligation PCR was described in Slebert P. D. et al. (Slebert P D et al. 1995. An improved PCR method for walking in uncloned genomic DNA. *Nucleic Acids Research* 23:1087-1088). Specific steps are as follows:

1) Extraction of Total DNA from *B. Thuringiensis* YBT-978

*B. thuringiensis* YBT-978 is inoculated on 5 ml LB culture medium using an inoculation loop under sterile conditions and is cultured overnight in 30° C. on a shaker at 200 rpm. Then, 50 μl of the culture is transferred under sterile conditions to 5 ml fresh LB culture medium, and incubate under same conditions till logarithmic growth phase. Collect the bacteria after centrifugation at 5000 rpm for 3 minutes. Rinse once with 1 ml STE. Add 100 μl solution I and 10 μl lysozyme (50 mg/ml) and allow for action for 30 minutes or above. Add 200 μl 2% SDS, and incubate with a water bath at 50-60° C. for 30 minutes. Add 200 μl 5 mol/L NaCl and mix. Add 500 μl phenol/chloroform/isopentyl alcohol (25:24:1 v/v) and centrifuge for 5 minutes at 12000 rpm. Collect the supernatant and repeat the extraction once or twice. Transfer the upper layer DNA solution to Eppendorf tubes and then add equal volumes of 95% ethanol. Set in room temperature for 5 minutes, and then centrifuge for 5 minutes at 12000 rpm. Use 200 μl 70% ethanol to rinse the precipitates once and freeze-dry the precipitates, then dissolve the freeze-dried precipitates in 50 μl TE solution.

2) Enzymatic Digestion of the Total DNA with Restriction Endonuclease and Ligation with Adaptor (1) Allow the prepared total DNA of *Bacillus thuringiensis* to be enzymatically digested by HpaI enzyme at 37° C. overnight (the enzymatic digestion system is 50 μl comprising about 1 μg total DNA); (2) Add 50 μl enzymatic digestion product into 250 μl phenol:chloroform:isopentyl alcohol (25:24:1 v/v), centrifuge at 12000 rpm for 5 minutes, transfer the upper layer DNA solution to Eppendorf tubes, add equal volumes of 95% ethanol, set at room temperature for 5 minutes, then centrifuge at 12000 rpm for 5 minutes. The precipitate is rinsed with 200 μl 70% ethanol once and then freeze-dried and dissolved in 50 μl sterilized water; (3) Mix equal volume of long and short adaptors (50 μM) (the sequence of long adaptor is: 5 GCTCGAGTCGACCGTGGTACGCGT-GTGTGAGCTCCCGGGATCCGGT-3' (SEQ ID NO: 4); the sequence of short adaptor is 5 ACCGGATC-$NH_2$-3') to give a 4 μl solution, which is incubated in 70° C. for 10 minutes; (4) 4 μl adaptor solution (25 μM), 10 μl the solution of the total DNA enzymatic digestion product (contains about 0.5 μg DNA), 8U T4 ligase, 2 μl T4 ligase buffer; and add water to make a 20 μl system. Ligate at 16° C. for 12 hours; (5) After heating at 60° C. for 5 minutes, the ligation system used as a template for PCR amplification;

3) Nested PCR and Sequencing

Two rounds of PCR amplification are carried out with the aforesaid ligation product.

Based on the sequenced N-terminal amino acid sequence, synthetic gene-specific primers which are abbreviated as 130P1 and 130P2 are designed. Moreover, synthetic adaptor primers abbreviated as AP1 and AP2 are designed based on the long adaptor sequence. The sequences of the primers are as follows:

```
130P1:
5-ATGGATATHMGNAATCARAAYAARTAYG-3      (SEQ ID NO: 5)

130P2:
5-AATAAATATGARGTWGTNTAYCCNGC-3        (SEQ ID NO: 6)

AP1:
5-GCTCGAGTCGACCGTGGTA-3               (SEQ ID NO: 7)

AP2:
5-GTACGCGTGTGTGAGCTCC-3               (SEQ ID NO: 8)
```

(H = A, C, or T; M-A or C; N = A, G, C, or T; R = A or G; Y = C or T; W = A or T)

(A) First round PCR. 25 μl reaction system contains: 2.5 μl 10×PCR reaction buffer, 1 μl dNTP (2.5 mM each), 0.5 μl adaptor primer AP1 (20 mM), 0.5 μl specific primer 130P1 (20 mM), 1 μl template (the above ligation product), 0.5 μl ExTaq enzyme. Add sterilized de-ionized water to make it to 25 μl. The PCR conditions are: 94° C., 1 minute for 1 cycle; 94° C., 1 minute, 52° C., 1 minute, 72° C., 1.5 minute for 25 cycles; 72° C., 5 minutes for 1 cycle. The first round PCR product is diluted 50-fold to give the amplification template for the second round of PCR.

(B) Second round PCR. 50 μl reaction system contains: 5 μl 10×PCR reaction buffer, 2 μl dNTP (2.5 mM each), 1 μl adaptor primer AP2 (20 mM), 1 μl specific primer 130P2 (20 mM), 1 μl template (the product of the first round of PCR), 1 μl ExTaq enzyme. Add sterilized de-ionized water to make it to 50 μl. The PCR reaction conditions are the same as aforesaid, except that the annealing temperature is 56° C.

(C) The products of the second round of PCR are recovered by PCR product recovering kit (purchased from Veta-Gene Company) and are then ligated to T-vector. The ligation product is used to transform *E. coli* E.DH5α. Perform PCR amplification to screen the transformants by using AP2 and 130P2 as primers and using single colony bacteria as the template. And sequence the exogenous fragments in positive transformant T-vector. The sequencing result is the sequence between position 19 to 491 of the nucleotide in SEQ ID NO:1.

Specific primers abbreviated as 130S1 and 130A1-2 are designed based on the above sequencing result. They are used to screen BAC genomic library containing the gene for crystal protein and various positive transformants, and size of the amplification product is 434 bp. The sequence of the primers are:

```
130S1-2:
TTCTAATACAACATCAAAGTATCCACTC    (SEQ ID NO: 9)

130A1-2:
GGTATCGTTCCAATACTAATTCTAAAC     (SEQ ID NO: 10)
```

3. The Cloning of Insecticidal Crystal Protein Gene cry7Ba1 of *B. thuringiensis* YBT-978

Figure 2:
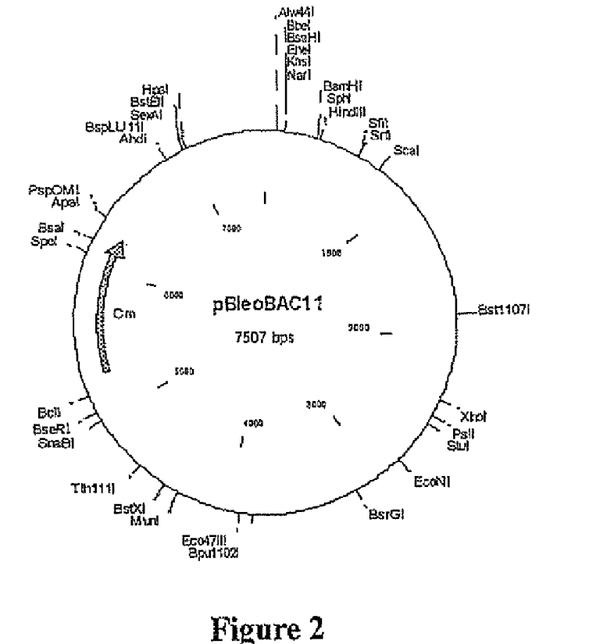
FIG. 2: Construction chart of BAC vector pBleoBAC11 of the example of the present invention

1) Construction of Genomic BAC Library of *B. thuringiensis* YBT-978 Bacterial Strain Use BAC library vector pBeloBAC11 (as shown in FIG. 2) to construct the genomic BAC library of *B. thuringiensis* YBT-978 according to the method disclosed by Luo and Wing (2003) (refer to Luo and Wing. 2003. An improved method for plant BAC library construction, p. 3-19. In Grotewold, Erich, Plant functional genomic: methods and protocols. Scientific and medical publishers/Humana Press, Totowa, USA).

That is, *B. thuringiensis* YBT-978 is allowed to grow in LB culture medium till mid-logarithmic growth phase, and then the bacteria is collected by centrifugation at 10000 rpm for 1 minute in clean and sterilized 50 ml centrifugation tubes. Add 1 ml TE buffer (1 mM EDTA, 10 mM Tris base, pH 8.0) to the collected bacteria, which is then lightly dispersed on an vibrator. Add about 40 ml TE buffer, set for 5 minutes and collect the bacteria by centrifugation at 10000 rpm for 1 minute. Set a 50 ml centrifugation tube containing the bacteria in warm water at 50° C. and add 1.5 ml TE25S (0.3 M sucrose, 25 mM EDTA, 25 mM Tris Base, pH 8.0), then mix well and add 1.5 ml 2% warmed gel (which is a low melting point gel and specialized for making embedding block, 0.1 g of such gel is dissolved in 5 ml TE25S). Mix well using an autopipette and add the mixture into molds for making embedding blocks, which are then cooled in a refrigerator at 4° C. to set the embedding blocks. The remaining steps, which include the enzymatic digestion of YBT-978 in the embedding blocks by HindIII and the recovery of enzymatic digestion products, the preparation of BAC library vector pBeloBAC11, the ligation of the enzymatic digestion products to the vectors and the qualification of the transformed DH10B and BAC libraries, are identical to the methods reported by Luo and Wing (2003).

2) Screening of BAC Genomic Library and Cloning of the Insecticidal Crystal Protein Gene cry7Ba1.

(A) Screening of BAC Genomic Library

PCR amplification is carried out by using 130S1 and 130A1 as primers and using BAC library single colony bacteria as the template. The reaction system is 25 μl, the formulation of which is identical to aforesaid. The reaction conditions are the same with aforesaid, except that the annealing temperature is 55° C. Positive clone EMB0491 is selected. Extract recombinant plasmid pBMB0491 according to the method disclosed by J. Sambrook et al. (J. Sambrook et al (2002). Molecular Cloning: A Laboratory Manual. 3rd Edition. Translated by Jin Dong-yan et al. Science Press. Beijing). Enzymatic digestion result indicates that pBMB0491 contains an about 60 kb fragment of YBT-978 genome.

(B) Acquisition of Insecticidal Crystal Protein Gene cry7Ba1

Figure 3:
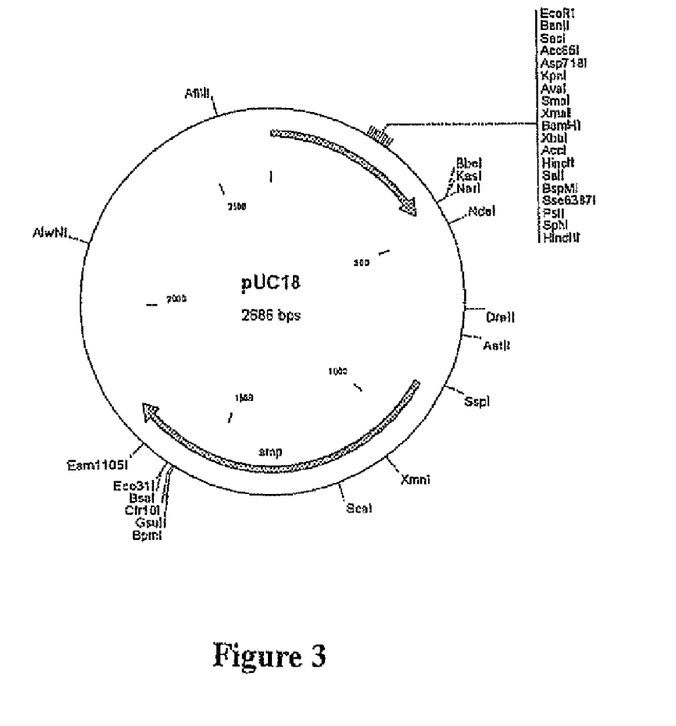
FIG. 3: Construction chart of cloning vector pUC18 constructed in the present invention

Use HindIII to complete enzymatically digest the YBT-978 genomic fragment in the positive clones. The enzymatic digestion product is ligated with cloning vector pUC18 (see FIG. 3) which is also complete enzymatically digested by HindIII. And the ligation product is used to transform *E. coli* DH5α. Primers numbered as 130S1-2 and 130A1-2 are again used as primers and transformant single colony bacteria is used as template to perform PCR amplification to screen positive transformant EMB0493, Extract recombinant plasmid pBMB0492 from EMB0493. Enzymatic digestion result indicates that pBMB0492 contains an about 16 kb fragment of YBT-978 genome. Further analysis showed the insecticidal crystal protein gene cry7Ba1 locates in the 5 kb XhoI fragment.

(C) Sequence Analysis on Insecticidal Crystal Protein Gene cry7Ba1 and Insecticidal Crystal Protein Cry7Ba1

Analyze the nucleotide sequence of 5 kb XhoI fragment in which the insecticidal crystal protein gene cry7Ba1 locates and obtain a sequence comprising 5235 bp, wherein 3465 bp are coding region. The coding sequence is shown as SEQ ID NO:1.

The said coding sequence may encode a polypeptide consisting of 1154 amino acids, i.e. insecticidal crystal protein Cry7Ba1, the molecular weight of which is deduced to be 130558 Da.

Searching and comparing this polypeptide with amino acid sequences of other known Cry and Cyt proteins in the GenBank gene database on the web at ncbi.nlm.nih.gov, it is discovered that, among all proteins publicly disclosed, the one which is closest to insecticidal crystal protein Cry7Ba1 is insecticidal crystal protein Cry7Ab2 (GenBank registration number: U04368), Cry7Ab1 (GenBank registration number: U04367) and CryAa1 (GenBank registration number: M64478), with the homology is 58.2%, 57.9% and 57.1% respectively. The homology of the sequence at the N-terminal half (position 1 to 658 amino acid in SEQ ID NO:2) is very low, which is the homology of 37.1%, 37.0% and 36.4% respectively. Said half is the part responsible for insecticidal activity and is essential and adequate for exerting insecticidal activity (Schnepf H E, Crickmore N, Rie J V, Lereclus D, Baum J, Feitelson J, Zeigler D R, Dean D H. 1998. *B. thuringiensis* and its pesticidal crystal proteins. *Microbiol Mol Biol Rev*, 62:775-806). From this it can be seen the insecticidal gene is a novel insecticidal gene. Therefore, International *B. thuringiensis* Gene Nomenclature Committee named the said insecticidal crystal protein gene as cry7Ba1 which is determined to be a model gene of cry7B gene. Moreover, the sequence is highly similar to the known proteins at the C-terminal half (i.e. position 659 to 1154 amino acids of SEQ ED NO:2), with the homology reaching 87.9%, 86.9% and 87.9% respectively. The sequence of this part is the functional structural domain for forming the parasporal crystal, which is not relevant to insecticidal activity.

It can be seen from the above sequence analysis that, among all disclosed proteins, the homology of the one which is closest to the insecticidal crystal protein Cry7Ba1 of the present invention is 58.2%, which does not exceed 80%. When the homology of the amino acid sequence of a certain protein to the insecticidal crystal protein Cry7Ba1 exceeds 80%, it is deemed as falling within the scope of insecticidal crystal protein Cry7Ba1 of the present invention. Similarly, among all disclosed proteins, the homology of the one which is closest to the N-terminal half (position 1 to 658 amino acids of SEQ ID NO:2) of the insecticidal crystal protein Cry7Ba1 of the present invention is 37.1%, which does not exceed 50%. When the homology of amino acid sequence of a protein to the N-terminal half (position 1 to 658 amino acids of SEQ ID NO:2) of insecticidal crystal protein Cry7Ba1 exceeds 50%, it is deemed as falling within the scope of insecticidal crystal protein Cry7Ba1 of the present invention.

4. Insecticidal Activity of Insecticidal Crystal Protein Cry7Ba1 of *B. Thuringiensis* YBT-978

Figure 4:
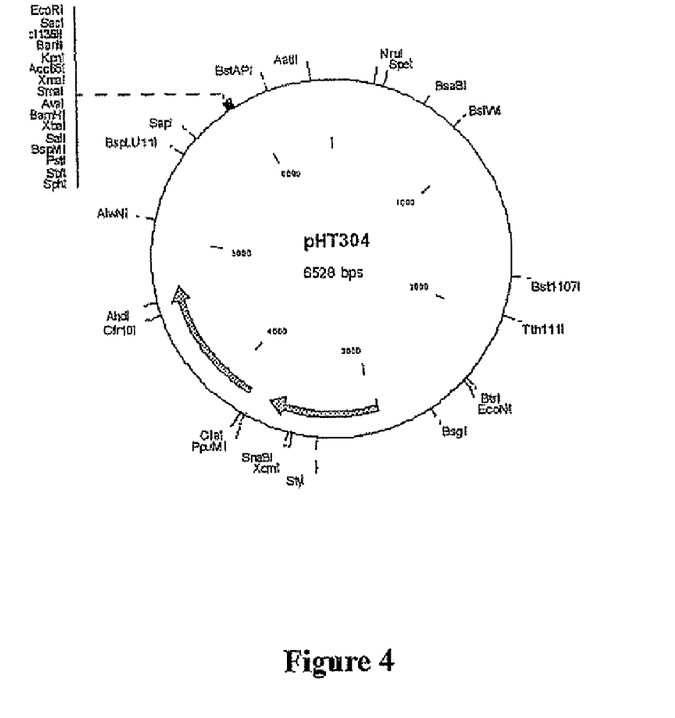
FIG. 4: Construction chart of the shuttle vector constructed in the example of the present invention
Figure 5:
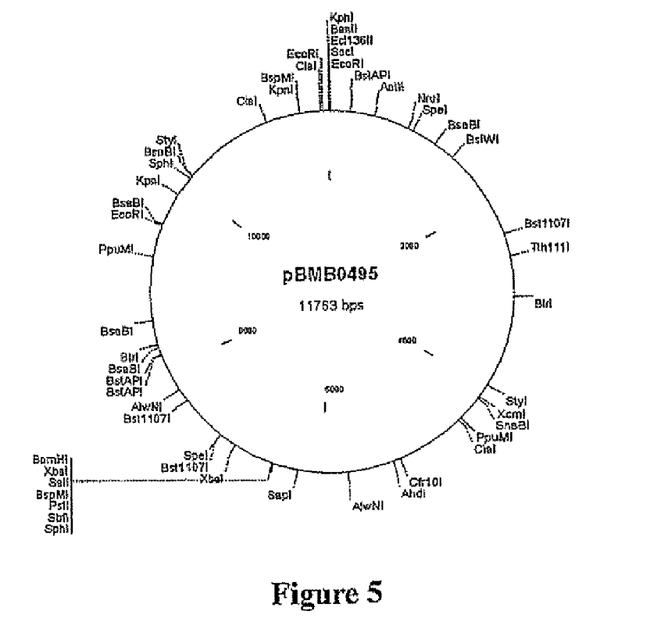
FIG. 5: Recombinant plasmid pBMB0495 constructed in the example of the present invention

5 kb XhoI fragment in which cry7Ba1 locates is transferred to *E. coli-B. thuringiensis* shuttle vector pHT304 (see FIG. 4, for origin of the vector, please refer to Arantes O and Lereclus D. 1991. Construction of cloning vectors for *B. thuringiensis*. Gene 108:115-119) to give a recombinant plasmid pBMB0495 (see FIG. 5). Then, pBMB0495 is transformed to an acrystalliferous mutant of *B. thuringiensis* CryB strain (for the origin of the strain, please refer to Wu D, Federici B A. 1993. A 20-kilodalton protein preserves cell viability and promotes CytA crystal formation during sporulation in *Bacillus thuringiensis*. *J. Bacteroil*., 175:5276-5280) using well established electroporation method (Wu Lan, Sun Ming, Yu Ziniu. A New Resolution Vector with cry1Ac10 Gene Based on *Bacillus thuringiensis* Transposon Tn4430. Acta Mcrobiologica Sinica. 2000, 40:264-269) to give recombinant bacteria BMB-0502.

(1) Expression of Insecticidal Crystal Protein Cry7Ba1

Figure 6:
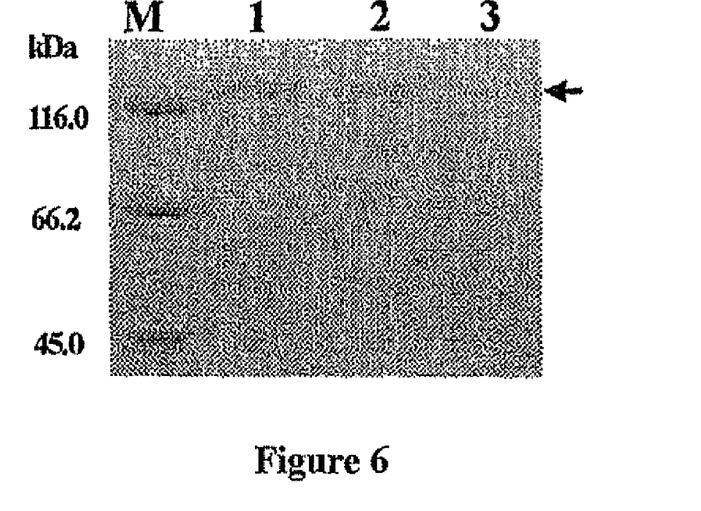
FIG. 6: SDS-PAGE electrophoresis analysis of *Bacillus thuringiensis* Cry7Ba1 parasporal crystal protein cloned in the present invention M: molecular weight markers
1: parasporal crystal protein of YBT-978 strain
2: parasporal crystal protein of BMB0502 strain
3: control BMB0503 strain

Activate BMB0502 by incubating it in LB culture medium (erythromycin can be added at a final concentration of 20 μg/ml) overnight. Then, it is transferred to ICPM culture medium (erythromycin can be added at a final concentration of 20 μg/ml), incubate until gemma completely mature and fall off. Collect the bacteria and rinse them with 0.5% NaCl and sterilized de-ionised water separately for 3 times. Re-mix fee bacteria with water at the ratio bacteria:sterilized de-ionised water=1:5; then add an equal volume of 2× loading buffer and mix well. Incubate in a boiling water bath for 3 to 5 minutes, then centrifuge at 12000 rpm for 5 minutes. Perform SDS-PAGE electrophoresis with the supernatants. For the formulation of 2× loading buffer and the procedure for performing SDS-PAGE electrophoresis, please refer to the method recited by Laemmli (Laemmli, UK. 1970. Digestion of structural proteins during the assembly of the head of bacteriophage T4. *Nature* (London) 227:680-685). As shown in FIG. 6, BMB0502 can form a 130 kDa crystal protein, the size of which is identical to YBT-978 of the starting strain, whilst negative control BMB0503 (which only contains the shuttle vector pHT304) does not form such a corresponding band.

(2) Crystal Morphology of Insecticidal Crystal Protein Cry7Ba1

Figure 7:
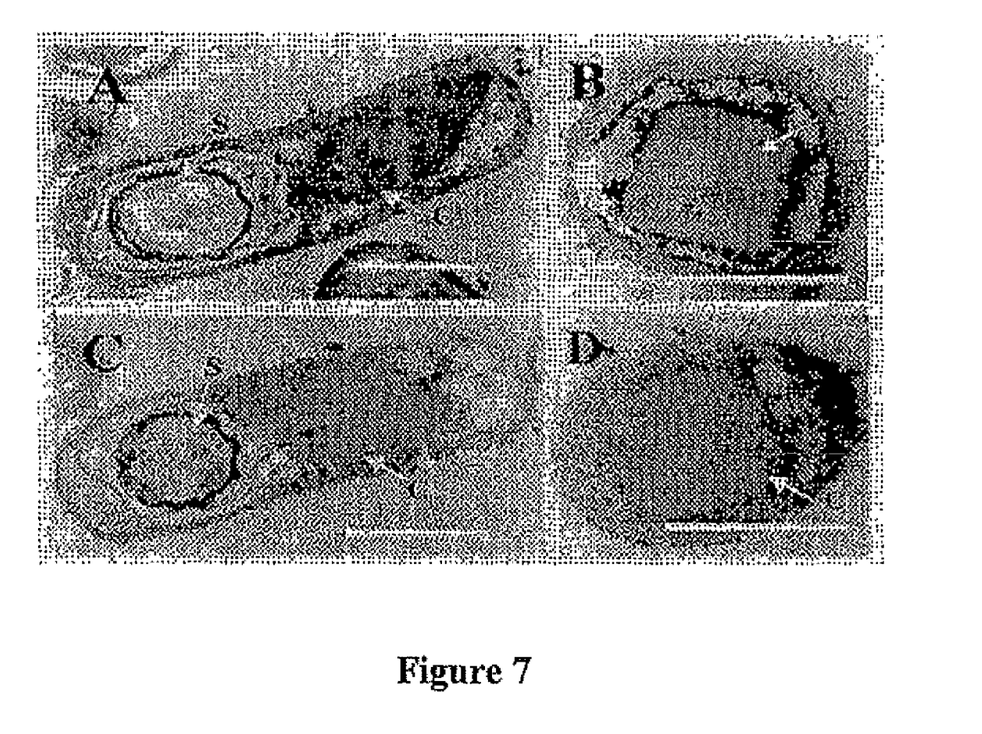
FIG. 7: Morphology of parasporal crystal produced by *Bacillus thuringiensis* YBT-978 and BMB0502 strains involved in the present invention (the line standard represents 1 μm)

Activate BMB0502 by incubating it in LB culture medium (erythromycin can be added at a final concentration of 20 μg/ml) overnight. Then, it is transferred to ICPM culture medium (erythromycin can be added at a final concentration of 20 μg/ml), incubate until gemma almost mature and fall off. Collect the bacteria and rinse them with sterilized de-ionised water once. Re-mix the bacteria with water at the ratio bacteria:sterilized de-ionised water=1:5. Prepare samples for transmission electron microscopy (TEM) and embed with Epon812. Make ultra-thin slices, perform transmission observation and photo taking at 80 kv. MBM0502 can form bi-pyramid shaped parasporal crystal which is shown in FIG. 7.

(3) Evaluation of Insecticidal Effect of Insecticidal Crystal Protein Cry7Ba1

Insecticidal effect of insecticidal crystal protein Cry7Ba1 is evaluated using third instar larvae of *Plutella xylostella*. Activate BMB0502 by incubating it in LB culture medium (erythromycin can be added at a final concentration of 20 μg/ml) overnight. Then, it is transferred to ICPM culture medium (erythromycin can be added at a final concentration of 20 μg/ml), incubate till gemma almost mature and fall off. Collect the bacteria and rinse them with sterilized de-ionised water once to give a parasporal crystal mixture. Perform bioassay using standard assay procedure (please refer to Shen Ju-qun, Wang Mian-ju, Yu Zi-niu (1990). Standard Procedure and Method for *Bacillus thuringiensis* formulations. Chinese Journal of Biological Control (Suppl.): 12-16). The bioassay is repeated once for each of the samples. Calculate $LC_{50}$. The results showed the insecticidal crystal protein Cry7Ba1 exerted very high toxicity against *Plutella xylostella* (as shown in Table 1). This means the Cry7Ba1 protein cloned in the present invention shows very high insecticidal activity against insects of the Lepidoptera Order.

TABLE 1

Experimental results from bioassay of the Cry7Ba1 protein cloned in the present invention against *Plutella xylostella*

| Time (Day) | Material | Regression equation | Regression coefficient | $LC_{50}$ value (95% confidence limit) (ng/ml) |
|---|---|---|---|---|
| 3 | BMB0502 | y = 0.9928x + 3.0334 | 0.9946 | 95.7 (93.9-97.5) |
| 5 | BMB0502 | y = 1.0554x + 3.3103 | 0.9901 | 39.9 (38.2-41.6) |

DESCRIPTION OF THE DRAWINGS

A, B: parasporal crystal morphology of YBT-978 strain;
C, D: parasporal crystal morphology of BMB0502 strain.

SPECIFIC EMBODIMENTS OF THE PRESENT INVENTION

The followings are examples showing the present invention. It should be noted that the examples only demonstrate the present invention but by no means limit the present invention. The various experimental procedures involved are standard techniques in the field of the invention. For the contents that are not specifically explained, skilled persons in the art can refer to various reference books, scientific articles, relevant manuals and handbooks that are available prior to the application date of the present invention to carry out the said contents.

Example 1

The Cloning of Insecticidal Crystal Protein Gene cry7Ba1 of *Bacillus thuringiensis* YBT-978

According to the method disclosed by Luo and Wing (2003) (refer to Luo and Wing. 2003. An improved method for plant BAC library construction, p. 3-19. In Grotewold, Erich, Plant functional genomic: methods and protocols. Scientific and medical publishers/Humana Press, Totowa, USA), BAC library vector pBeloBAC11 was used to construct genomic BAC library of *Bacillus thuringiensis* YBT-978 strain (for the source of the bacterial strain, please refer to Dai J et al. 1996. *Bacillus thuringiensis* subsp. *huazhongensis*, serotype H40, isolated from soils in the People's Republic of China, Letters in Applied Microbiology. 22(1): 42-45). Primers numbered as 130S1-2 and 130A1-2 were used as primers and BAC library single colony bacteria is used as the template to perform PCR amplification. Positive clone EMB0491 was selected. HindIII was used to complete enzymatically digest the YBT-978 genomic fragment in the positive clones. The enzymatic digestion product was ligated with cloning vector pUC18 which was also completely enzymatically digested by HindIII to transform *E. coli* DH5α. Primers numbered as 130S1-2 and 130A1-2 were again used as primers and transformant single colony bacteria is used as template to perform PCR amplification to screen positive transformant EMB0493. Recombinant plasmid pBMB0492 was extracted from EMB0493. Enzymatic digestion result revealed that pBMB0492 contains a fragment of about 16 kb of YBT-978 genome. Further analysis showed the insecticidal crystal protein gene cry7Ba1 locates in the 5 kb XhoI fragment.

Example 2

Sequence Analysis on Insecticidal Crystal Protein Gene cry7Ba1 of *Bacillus thuringiensis* YBT-978

The nucleotide sequence of the 5 kb XhoI fragment, in which the insecticidal crystal protein gene cry7Ba1 locates, was analyzed. The result was that it was a sequence comprising 5235 bp, wherein 3465 bp were the coding sequence. The coding sequence is shown as SEQ BD NO:1.

The said coding sequence might encode a polypeptide consisting of 1154 amino acids, the molecular weight of which was deduced to be 130558 Da.

Comparing this polypeptide with amino acid sequences of other known Cry and Cyt proteins, it was discovered that it was closest to Cry7Ab2, Cry7Ab1 and CryAa1, with the homology being 58.2%, 57.9% and 57.1% respectively. The homology of the sequence at the N-terminal half (position 1 to 658 amino acid in SEQ ID NO:1) was very low, with the homology being 37.1%, 37.0% and 36.4% respectively. As the polypeptide was similar to Cry7A insecticidal crystal protein, it was named by the International *Bacillus thuringiensis* Gene Nomenclature Committee as cry7Ba1.

Example 3

Expression of Insecticidal Crystal Protein Gene cry7Ba1

5 kb XhoI fragment, in which cry7Ba1 locates, was transferred to *E. coli-B. thuringiensis* shuttle vector pHT304 (for origin of the vector, please refer to Arantes O and Lereclus D. 1991. Construction of cloning vectors for *Bacillus thuringiensis*. Gene 108:115-119) to give recombinant plasmid pBMB0495. Then, pBMB0495 was transferred to an acrystalliferous mutant of *Bacillus thuringiensis* CryB strain (for the origin of the strain, please refer to Wu D, Federici B A. 1993, A 20-kilodalton protein preserves cell viability and promotes CytA crystal formation during sporulation in *Bacillus thuringiensis*. J. Bacteroil., 175:5276-5280) using well established electroporation method (Wu Lan, Sun Ming, Yu Ziniu. A New Resolution Vector with cry1Ac10 Gene Based on *Bacillus thuringiensis* Transposon Tn4430. Acta Microbiologica Sinica. 2000, 40:264-269) to give recombinant bacteria BMB-0502.

The above recombinant bacteria named as BMB0502 was activated by incubating it in LB culture medium (erythromycin could be added at a final concentration of 20 μg/ml) overnight. Then, it was transferred to ICPM culture medium (erythromycin could be added at a final concentration of 20 μg/ml), incubation was carried out until gemma completely matured and fell off. The bacteria was collected and rinsed with 0.5% NaCl and sterilized de-ionised water separately for 3 times. The bacteria was re-mixed with water at the ratio bacteria:sterilized de-ionised water=1:5, then an equal volume of 2× loading buffer was added and mixed well. The mixture was treated in a boiling water bath for 3 to 5 minutes, then centrifuged at 12000 rpm for 5 minutes. SDS-PAGE electrophoresis was performed for the supernatants. For the formulation of 2× loading buffer and the procedure for performing SDS-PAGE electrophoresis, please refer to the method recited by Laemmli (Laemmli, UK. 1970. Digestion of structural proteins during the assembly of the head of bacteriophage T4. *Nature* (London) 227:680-685). As shown in FIG. 6, BMB0502 forms a 130 kDa crystal protein, the size of which was identical to YBT-978 of the starting strain, whilst the negative control BMB0503 (which only contained the shuttle vector pHT304) did not form such a corresponding band.

Example 4

Insecticidal Effect of Insecticidal Crystal Protein Cry7Ba1

Insecticidal effect of insecticidal crystal protein Cry7Ba1 was evaluated using third instar larvae of *Plutella xylostella*. BMB0502 was activated by incubating it in LB culture medium (erythromycin could be added at a final concentration of 20 μg/ml) overnight. Then, it was transferred to ICPM culture medium (erythromycin could be added at a final concentration of 20 μg/ml), incubation was carried out until gemma almost matured and fell off. The bacteria was collected and rinsed with sterilized de-ionised water once to give a parasporal crystal mixture. Bioassay was performed using standard assay procedure (please refer to Shen Ju-qun, Wang Mian-ju, Yu Zi-niu (1990). Standard Procedure and Method for *Bacillus thuringiensis* formulations. Chinese Journal of Biological Control (Suppl.): 12-16). The bioassay was repeated once for each of the samples. $LC_{50}$ was calculated. The results showed the insecticidal crystal protein Cry7Ba1 exerted very high toxicity against *Plutella xylostella*. This means the Cry7Ba1 protein cloned in the present invention showed very high insecticidal activity against insects of the Lepidoptera, The effects achieved by carrying out the example was shown in Table 1.

The invention claimed is:

1. An isolated insecticidal crystal protein gene from *Bacillus thuringiensis*, wherein said gene encodes a Cry7Ba1 protein comprising the amino acid sequence shown in SEQ ID NO: 2.

2. The isolated insecticidal crystal protein gene from *Bacillus thuringiensis* of claim 1, wherein said gene comprises the nucleotide sequence shown in SEQ ID NO: 1.

3. An isolated insecticidal crystal protein gene from *Bacillus thuringiensis*, wherein said gene encodes a Cry7Ba1 protein comprising the partial sequence numbered 1 to 658 of SEQ ID NO: 2.

4. A recombinant DNA construct comprising the insecticidal crystal protein gene according to any one of claims 1-3.

5. A micro-organism comprising the recombinant DNA construct of claim 4.

6. A *Bacillus thuringiensis* insecticidal crystal protein comprising the amino acid sequence shown in SEQ ID NO: 2.

7. A *Bacillus thuringiensis* insecticidal crystal protein comprising the partial sequence numbered 1 to 658 of SEQ ID NO:2.

8. An insecticidal fragment of a Cry7Ba1 protein which comprises the amino acid sequence as shown in SEQ ID NO: 2.

9. A plant cell transformed with a nucleic acid encoding the insecticidal fragment of claim 8.

* * * * *

SEQUENCE LISTING

```
<160> NUMBER OF SEQ ID NOS: 10

<210> SEQ ID NO 1
<211> LENGTH: 3465
<212> TYPE: DNA
<213> ORGANISM: Bacillus thuringiensis
<220> FEATURE:
<221> NAME/KEY: CDS
<222> LOCATION: (1)..(3465)

<400> SEQUENCE: 1 atg gat ata aga aat caa aat aaa tat gaa gta gta tac cca gca ata      48
Met Asp Ile Arg Asn Gln Asn Lys Tyr Glu Val Val Tyr Pro Ala Ile
1               5                   10                  15 aat gaa aca act tct aat aca aca tca aag tat cca ctc gca agt gat      96
Asn Glu Thr Thr Ser Asn Thr Thr Ser Lys Tyr Pro Leu Ala Ser Asp
                20                  25                  30 cca atc aaa caa tat caa aat atg aat tat aaa gat agt ttg aat ata     144
Pro Ile Lys Gln Tyr Gln Asn Met Asn Tyr Lys Asp Ser Leu Asn Ile
            35                  40                  45 att gag ggg aat aac gta atc act cca gta tct gga act gct gtt ttg     192
Ile Glu Gly Asn Asn Val Ile Thr Pro Val Ser Gly Thr Ala Val Leu
        50                  55                  60 gca act gca agg aaa att ggt ggt aag atc gtt aag gct ata ggg gaa     240
Ala Thr Ala Arg Lys Ile Gly Gly Lys Ile Val Lys Ala Ile Gly Glu
65                  70                  75                  80 caa atc ttg tct aaa atc ttg aaa gag att ctt gat tat tta tgg ccg     288
Gln Ile Leu Ser Lys Ile Leu Lys Glu Ile Leu Asp Tyr Leu Trp Pro
                85                  90                  95 tct tca agc tcg tcc aat tca tgg gaa gag atg atg aag gaa gta gag     336
Ser Ser Ser Ser Ser Asn Ser Trp Glu Glu Met Met Lys Glu Val Glu
                100                 105                 110 tat ctt att gat aaa aaa ata gag gaa tat gca aga aat aag gca ctt     384
Tyr Leu Ile Asp Lys Lys Ile Glu Glu Tyr Ala Arg Asn Lys Ala Leu
            115                 120                 125 gcg gtt ttg gaa gga ata gga aat gct gta gaa tcc tat tat agt gca     432
Ala Val Leu Glu Gly Ile Gly Asn Ala Val Glu Ser Tyr Tyr Ser Ala
        130                 135                 140 tta gaa gcg tgg gaa tta gaa tct agt gaa cgt agt tta gaa tta gta     480
Leu Glu Ala Trp Glu Leu Glu Ser Ser Glu Arg Ser Leu Glu Leu Val
145                 150                 155                 160 ttg gaa cga tat cag ttt gcg gtg cag ttt gca aga agt tca atg cca     528
Leu Glu Arg Tyr Gln Phe Ala Val Gln Phe Ala Arg Ser Ser Met Pro
```

-continued

```
                165                 170                 175
tca ttt gcg att ata aat tat gaa att ccc tta tta gca aca tat gca    576
Ser Phe Ala Ile Ile Asn Tyr Glu Ile Pro Leu Leu Ala Thr Tyr Ala
            180                 185                 190 aat gct gca aat gtt cat tta ctt tta atg aga gat ata caa ata tac    624
Asn Ala Ala Asn Val His Leu Leu Leu Met Arg Asp Ile Gln Ile Tyr
            195                 200                 205 ggg gat aga tgg gga ata tct caa aat gat atg aat ctc ttc tta aaa    672
Gly Asp Arg Trp Gly Ile Ser Gln Asn Asp Met Asn Leu Phe Leu Lys
        210                 215                 220 gaa caa gaa ata tac acg tct gaa tat tcg gaa cat tgc gta aag tgg    720
Glu Gln Glu Ile Tyr Thr Ser Glu Tyr Ser Glu His Cys Val Lys Trp
225                 230                 235                 240 tat aat gag gga tta aat caa ttg aaa act aaa ggt ggc gca agt ggt    768
Tyr Asn Glu Gly Leu Asn Gln Leu Lys Thr Lys Gly Gly Ala Ser Gly
                245                 250                 255 tta gtt tgg gag aat tat aac agt ttt cgt aca gaa atg aca att atg    816
Leu Val Trp Glu Asn Tyr Asn Ser Phe Arg Thr Glu Met Thr Ile Met
            260                 265                 270 gta tta gat ctt gta gct ata ttt cca gcc tac aat atg agc aaa tat    864
Val Leu Asp Leu Val Ala Ile Phe Pro Ala Tyr Asn Met Ser Lys Tyr
            275                 280                 285 cct ata gaa tca aca gta gaa tta aca aga aca att tat aca gat cca    912
Pro Ile Glu Ser Thr Val Glu Leu Thr Arg Thr Ile Tyr Thr Asp Pro
        290                 295                 300 ctt ggt tac aca ggg tat agc aat gat gaa cat ccc aca tat tat tct    960
Leu Gly Tyr Thr Gly Tyr Ser Asn Asp Glu His Pro Thr Tyr Tyr Ser
305                 310                 315                 320 tct gca aaa cca ttt tca tca ata gag agt aga gcc gta cta gca ccc   1008
Ser Ala Lys Pro Phe Ser Ser Ile Glu Ser Arg Ala Val Leu Ala Pro
                325                 330                 335 tca tta ttc aaa tgg atc act caa ctt gaa gta tat aca aaa aaa tac   1056
Ser Leu Phe Lys Trp Ile Thr Gln Leu Glu Val Tyr Thr Lys Lys Tyr
            340                 345                 350 agc tac tct tcc caa tat act acg ttg tgg act gga cta aga gtg att   1104
Ser Tyr Ser Ser Gln Tyr Thr Thr Leu Trp Thr Gly Leu Arg Val Ile
            355                 360                 365 gct cag cct act aaa gat ttt act gat act gta tat gat tac gga agt   1152
Ala Gln Pro Thr Lys Asp Phe Thr Asp Thr Val Tyr Asp Tyr Gly Ser
        370                 375                 380 tct tcg ggt tct gag aac aag gat gtc ttt gac ctt tat ggc aat gat   1200
Ser Ser Gly Ser Glu Asn Lys Asp Val Phe Asp Leu Tyr Gly Asn Asp
385                 390                 395                 400 gta tat gac aca caa agt gtt gtt tca tcg tat aag cct aca ggt ggt   1248
Val Tyr Asp Thr Gln Ser Val Val Ser Ser Tyr Lys Pro Thr Gly Gly
                405                 410                 415 ggc cat ttt ggg gtt cct cag ttt aga tta ttc tgg att act aaa tct   1296
Gly His Phe Gly Val Pro Gln Phe Arg Leu Phe Trp Ile Thr Lys Ser
            420                 425                 430 aat ggg cta aga gaa caa att ttt aat tat gcg aat aat atg ggt tct   1344
Asn Gly Leu Arg Glu Gln Ile Phe Asn Tyr Ala Asn Asn Met Gly Ser
            435                 440                 445 tac agt gcg tat agg ttt agt aag gac gaa tta cca ata gaa ttg ttg   1392
Tyr Ser Ala Tyr Arg Phe Ser Lys Asp Glu Leu Pro Ile Glu Leu Leu
        450                 455                 460 cag cca cct ctt ttt gga gat ata gag gaa tac agt cat agg tta agt   1440
Gln Pro Pro Leu Phe Gly Asp Ile Glu Glu Tyr Ser His Arg Leu Ser
465                 470                 475                 480 cac gtt tca gag gta att aaa gat tat ggt gaa gga atc att cct gta   1488
His Val Ser Glu Val Ile Lys Asp Tyr Gly Glu Gly Ile Ile Pro Val
```

```
                His Val Ser Glu Val Ile Lys Asp Tyr Gly Glu Gly Ile Ile Pro Val
                                485                 490                 495 tta ggt tgg aca cat gta agt gta act cgt gac aat aga att tat cca              1536
Leu Gly Trp Thr His Val Ser Val Thr Arg Asp Asn Arg Ile Tyr Pro
            500                 505                 510 gat aag att aca caa ctt cca gcg gta aaa atg tat gag tta cta agc              1584
Asp Lys Ile Thr Gln Leu Pro Ala Val Lys Met Tyr Glu Leu Leu Ser
            515                 520                 525 tca gcc gtt gtt gta aaa gga cct gga ttt aca ggt gga gat tta gtt              1632
Ser Ala Val Val Val Lys Gly Pro Gly Phe Thr Gly Gly Asp Leu Val
        530                 535                 540 aag aga acg ggc aat ggt ggc att gga cat ttt aat gtt agt gta gag              1680
Lys Arg Thr Gly Asn Gly Gly Ile Gly His Phe Asn Val Ser Val Glu
545                 550                 555                 560 tcc cct ggt act cag agg tat cgc ctg aga ata cgt tat agt tca gag              1728
Ser Pro Gly Thr Gln Arg Tyr Arg Leu Arg Ile Arg Tyr Ser Ser Glu
                565                 570                 575 gtt agt gga gta ttt cat atg caa att aac gat ata gaa act att cag              1776
Val Ser Gly Val Phe His Met Gln Ile Asn Asp Ile Glu Thr Ile Gln
            580                 585                 590 gga gaa ttt agt agt act gct gat tca aca agt act ctg tca agc gaa              1824
Gly Glu Phe Ser Ser Thr Ala Asp Ser Thr Ser Thr Leu Ser Ser Glu
            595                 600                 605 gca ttt caa ctt aga gaa tac tcc act acc ttc acg ttt cca aca aat              1872
Ala Phe Gln Leu Arg Glu Tyr Ser Thr Thr Phe Thr Phe Pro Thr Asn
        610                 615                 620 atg aca aag ata aag gta tct tta ggt gct att gaa ggt gca gga gga              1920
Met Thr Lys Ile Lys Val Ser Leu Gly Ala Ile Glu Gly Ala Gly Gly
625                 630                 635                 640 ttc tat tta gat aga att gaa ttc att cca gta gat gaa aat cac gat              1968
Phe Tyr Leu Asp Arg Ile Glu Phe Ile Pro Val Asp Glu Asn His Asp
                645                 650                 655 aac aga gta aca cta gaa aaa gca cag aaa gcc gtg aat gcc ttg ttt              2016
Asn Arg Val Thr Leu Glu Lys Ala Gln Lys Ala Val Asn Ala Leu Phe
            660                 665                 670 aca gcg gga aga aac gca cta caa aca gat gtg aca gat tac aaa gta              2064
Thr Ala Gly Arg Asn Ala Leu Gln Thr Asp Val Thr Asp Tyr Lys Val
            675                 680                 685 gat cag gtt tcc att tta gtg gat tgt gta tca ggg gag tta tat cca              2112
Asp Gln Val Ser Ile Leu Val Asp Cys Val Ser Gly Glu Leu Tyr Pro
        690                 695                 700 aat gag aaa cgc gaa cta ctc agt tta gtc aaa tac gca aaa cgt ttg              2160
Asn Glu Lys Arg Glu Leu Leu Ser Leu Val Lys Tyr Ala Lys Arg Leu
705                 710                 715                 720 agc tat tct cgt aat tta ctc cta gat cca aca ttc gat tct att aat              2208
Ser Tyr Ser Arg Asn Leu Leu Leu Asp Pro Thr Phe Asp Ser Ile Asn
                725                 730                 735 tcg tca gat gag aat ggc tgg tac gga agt aat ggt att gca att gga              2256
Ser Ser Asp Glu Asn Gly Trp Tyr Gly Ser Asn Gly Ile Ala Ile Gly
            740                 745                 750 aat ggg aac ttt gta ttc aaa gga aac tat tta att ttc tca ggt acc              2304
Asn Gly Asn Phe Val Phe Lys Gly Asn Tyr Leu Ile Phe Ser Gly Thr
            755                 760                 765 aat gat aca caa tac cca acg tat ctc tat caa aaa att gat gaa tcc              2352
Asn Asp Thr Gln Tyr Pro Thr Tyr Leu Tyr Gln Lys Ile Asp Glu Ser
        770                 775                 780 aag ctc aaa gaa tat aca cgc tat aaa ctg aga gga ttt atc gaa aat              2400
Lys Leu Lys Glu Tyr Thr Arg Tyr Lys Leu Arg Gly Phe Ile Glu Asn
785                 790                 795                 800
```

-continued

| | |
|---|---|
| agt caa gat tta gaa gca tat gtg att cgc tat gat gca aaa cat gaa<br>Ser Gln Asp Leu Glu Ala Tyr Val Ile Arg Tyr Asp Ala Lys His Glu<br>             805                    810                    815 | 2448 |
| aca ttg gat gta tcc aat aat cta ttg ccg gat att tct cct gta aat<br>Thr Leu Asp Val Ser Asn Asn Leu Leu Pro Asp Ile Ser Pro Val Asn<br>             820                    825                    830 | 2496 |
| gca tgc gga gaa cca aat cgt tgt gct gca tta caa tac ctg gat gaa<br>Ala Cys Gly Glu Pro Asn Arg Cys Ala Ala Leu Gln Tyr Leu Asp Glu<br>             835                    840                    845 | 2544 |
| aat cca agg tta gaa tgt agt tcg ata caa gac ggt att tta tct gat<br>Asn Pro Arg Leu Glu Cys Ser Ser Ile Gln Asp Gly Ile Leu Ser Asp<br>850                       855                    860 | 2592 |
| tcg cat tcg ttc tct ctc aat ata gat aca ggt tct att gat ttc aat<br>Ser His Ser Phe Ser Leu Asn Ile Asp Thr Gly Ser Ile Asp Phe Asn<br>865                       870                    875                    880 | 2640 |
| gag aac gta gga att tgg gtg ttg ttt aaa att tcc aca ccg gaa ggg<br>Glu Asn Val Gly Ile Trp Val Leu Phe Lys Ile Ser Thr Pro Glu Gly<br>                   885                    890                    895 | 2688 |
| tat gcg aaa ttt gga aac cta gaa gtg att gaa gat agc cca gtc att<br>Tyr Ala Lys Phe Gly Asn Leu Glu Val Ile Glu Asp Ser Pro Val Ile<br>             900                    905                    910 | 2736 |
| gga gaa gca tta gcc cgt gta aaa cgc caa gaa acg aag tgg cga aac<br>Gly Glu Ala Leu Ala Arg Val Lys Arg Gln Glu Thr Lys Trp Arg Asn<br>             915                    920                    925 | 2784 |
| aag ttg aca caa ctg cga acg gaa aca caa gcg att tat aca cga gca<br>Lys Leu Thr Gln Leu Arg Thr Glu Thr Gln Ala Ile Tyr Thr Arg Ala<br>             930                    935                    940 | 2832 |
| aaa caa gcc att gat aat gta ttc aca aat gca cag gac tct cac tta<br>Lys Gln Ala Ile Asp Asn Val Phe Thr Asn Ala Gln Asp Ser His Leu<br>945                       950                    955                    960 | 2880 |
| aaa ata ggt acg aca ttt gcg gca att gtg gct gcg cga aag att gtc<br>Lys Ile Gly Thr Thr Phe Ala Ala Ile Val Ala Ala Arg Lys Ile Val<br>                   965                    970                    975 | 2928 |
| caa tcc ata cgc gaa gcg tat atg tca tgg tta tca atc gtt cca ggt<br>Gln Ser Ile Arg Glu Ala Tyr Met Ser Trp Leu Ser Ile Val Pro Gly<br>             980                    985                    990 | 2976 |
| gta aat tat cct att ttt aca gag ttg aat gag aga gta cag cga gca<br>Val Asn Tyr Pro Ile Phe Thr Glu Leu Asn Glu Arg Val Gln Arg Ala<br>             995                   1000                1005 | 3024 |
| ttt caa tta tat gat gta cgg aat gtc gtg cgt aat ggc cga ttc<br>Phe Gln Leu Tyr Asp Val Arg Asn Val Val Arg Asn Gly Arg Phe<br>1010                      1015                    1020 | 3069 |
| ctg aat gga gta tcg gat tgg att gtg aca tct gat gta aag gta<br>Leu Asn Gly Val Ser Asp Trp Ile Val Thr Ser Asp Val Lys Val<br>1025                      1030                    1035 | 3114 |
| caa gaa gaa aat ggg aac aat gta tta gtt ctt tcc aat tgg gat<br>Gln Glu Glu Asn Gly Asn Asn Val Leu Val Leu Ser Asn Trp Asp<br>1040                      1045                    1050 | 3159 |
| gcg caa gta tta caa tgt ctg aag ctc tat caa gat cgc gga tat<br>Ala Gln Val Leu Gln Cys Leu Lys Leu Tyr Gln Asp Arg Gly Tyr<br>1055                      1060                    1065 | 3204 |
| atc ttg cgt gta acg gca cgt aaa gaa gga ttg gga gaa gga tat<br>Ile Leu Arg Val Thr Ala Arg Lys Glu Gly Leu Gly Glu Gly Tyr<br>1070                      1075                    1080 | 3249 |
| att aca att acg gat gaa gaa ggg cat aca gat caa ttg aca ttt<br>Ile Thr Ile Thr Asp Glu Glu Gly His Thr Asp Gln Leu Thr Phe<br>1085                      1090                    1095 | 3294 |
| ggc aca tgt gag gaa ata gat gca tct aac acg ttc gta acc aca<br>Gly Thr Cys Glu Glu Ile Asp Ala Ser Asn Thr Phe Val Thr Thr<br>1100                      1105                    1110 | 3339 |

-continued

```
ggt tat att aca aaa gaa cta gaa ttt ttc cca gat aca gag aaa      3384
Gly Tyr Ile Thr Lys Glu Leu Glu Phe Phe Pro Asp Thr Glu Lys
    1115                1120                1125
gtg cgt ata gaa att ggg gaa aca gaa gga acc ttc cag gta gaa      3429
Val Arg Ile Glu Ile Gly Glu Thr Glu Gly Thr Phe Gln Val Glu
    1130                1135                1140
agt ata gag tta ttt ttg atg gaa gat cta tgt taa                  3465
Ser Ile Glu Leu Phe Leu Met Glu Asp Leu Cys
    1145                1150

<210> SEQ ID NO 2
<211> LENGTH: 1154
<212> TYPE: PRT
<213> ORGANISM: Bacillus thuringiensis

<400> SEQUENCE: 2

Met Asp Ile Arg Asn Gln Asn Lys Tyr Glu Val Val Tyr Pro Ala Ile
1               5                   10                  15

Asn Glu Thr Thr Ser Asn Thr Thr Ser Lys Tyr Pro Leu Ala Ser Asp
            20                  25                  30

Pro Ile Lys Gln Tyr Gln Asn Met Asn Tyr Lys Asp Ser Leu Asn Ile
        35                  40                  45

Ile Glu Gly Asn Asn Val Ile Thr Pro Val Ser Gly Thr Ala Val Leu
    50                  55                  60

Ala Thr Ala Arg Lys Ile Gly Gly Lys Ile Val Lys Ala Ile Gly Glu
65                  70                  75                  80

Gln Ile Leu Ser Lys Ile Leu Lys Glu Ile Leu Asp Tyr Leu Trp Pro
                85                  90                  95

Ser Ser Ser Ser Ser Asn Ser Trp Glu Glu Met Met Lys Glu Val Glu
            100                 105                 110

Tyr Leu Ile Asp Lys Lys Ile Glu Glu Tyr Ala Arg Asn Lys Ala Leu
        115                 120                 125

Ala Val Leu Glu Gly Ile Gly Asn Ala Val Glu Ser Tyr Tyr Ser Ala
    130                 135                 140

Leu Glu Ala Trp Glu Leu Glu Ser Ser Glu Arg Ser Leu Glu Leu Val
145                 150                 155                 160

Leu Glu Arg Tyr Gln Phe Ala Val Gln Phe Ala Arg Ser Ser Met Pro
                165                 170                 175

Ser Phe Ala Ile Ile Asn Tyr Glu Ile Pro Leu Leu Ala Thr Tyr Ala
            180                 185                 190

Asn Ala Ala Asn Val His Leu Leu Leu Met Arg Asp Ile Gln Ile Tyr
        195                 200                 205

Gly Asp Arg Trp Gly Ile Ser Gln Asn Asp Met Asn Leu Phe Leu Lys
    210                 215                 220

Glu Gln Glu Ile Tyr Thr Ser Glu Tyr Ser Glu His Cys Val Lys Trp
225                 230                 235                 240

Tyr Asn Glu Gly Leu Asn Gln Leu Lys Thr Lys Gly Gly Ala Ser Gly
                245                 250                 255

Leu Val Trp Glu Asn Tyr Asn Ser Phe Arg Thr Glu Met Thr Ile Met
            260                 265                 270

Val Leu Asp Leu Val Ala Ile Phe Pro Ala Tyr Asn Met Ser Lys Tyr
        275                 280                 285

Pro Ile Glu Ser Thr Val Glu Leu Thr Arg Thr Ile Tyr Thr Asp Pro
    290                 295                 300

Leu Gly Tyr Thr Gly Tyr Ser Asn Asp Glu His Pro Thr Tyr Tyr Ser
```

-continued

```
            305                 310                 315                 320
        Ser Ala Lys Pro Phe Ser Ser Ile Glu Ser Arg Ala Val Leu Ala Pro
                        325                 330                 335
        Ser Leu Phe Lys Trp Ile Thr Gln Leu Glu Val Tyr Thr Lys Lys Tyr
                        340                 345                 350
        Ser Tyr Ser Ser Gln Tyr Thr Thr Leu Trp Thr Gly Leu Arg Val Ile
                        355                 360                 365
        Ala Gln Pro Thr Lys Asp Phe Thr Asp Thr Val Tyr Asp Tyr Gly Ser
                        370                 375                 380
        Ser Ser Gly Ser Glu Asn Lys Asp Val Phe Asp Leu Tyr Gly Asn Asp
        385                 390                 395                 400
        Val Tyr Asp Thr Gln Ser Val Val Ser Ser Tyr Lys Pro Thr Gly Gly
                        405                 410                 415
        Gly His Phe Gly Val Pro Gln Phe Arg Leu Phe Trp Ile Thr Lys Ser
                        420                 425                 430
        Asn Gly Leu Arg Glu Gln Ile Phe Asn Tyr Ala Asn Met Gly Ser
                        435                 440                 445
        Tyr Ser Ala Tyr Arg Phe Ser Lys Asp Glu Leu Pro Ile Glu Leu Leu
                        450                 455                 460
        Gln Pro Pro Leu Phe Gly Asp Ile Glu Glu Tyr Ser His Arg Leu Ser
        465                 470                 475                 480
        His Val Ser Glu Val Ile Lys Asp Tyr Gly Glu Gly Ile Ile Pro Val
                        485                 490                 495
        Leu Gly Trp Thr His Val Ser Val Thr Arg Asp Asn Arg Ile Tyr Pro
                        500                 505                 510
        Asp Lys Ile Thr Gln Leu Pro Ala Val Lys Met Tyr Glu Leu Leu Ser
                        515                 520                 525
        Ser Ala Val Val Lys Gly Pro Gly Phe Thr Gly Gly Asp Leu Val
                        530                 535                 540
        Lys Arg Thr Gly Asn Gly Ile Gly His Phe Asn Val Ser Val Glu
        545                 550                 555                 560
        Ser Pro Gly Thr Gln Arg Tyr Arg Leu Arg Ile Arg Tyr Ser Ser Glu
                        565                 570                 575
        Val Ser Gly Val Phe His Met Gln Ile Asn Asp Ile Glu Thr Ile Gln
                        580                 585                 590
        Gly Glu Phe Ser Ser Thr Ala Asp Ser Thr Ser Thr Leu Ser Ser Glu
                        595                 600                 605
        Ala Phe Gln Leu Arg Glu Tyr Ser Thr Thr Phe Thr Phe Pro Thr Asn
                        610                 615                 620
        Met Thr Lys Ile Lys Val Ser Leu Gly Ala Ile Glu Gly Ala Gly Gly
        625                 630                 635                 640
        Phe Tyr Leu Asp Arg Ile Glu Phe Ile Pro Val Asp Glu Asn His Asp
                        645                 650                 655
        Asn Arg Val Thr Leu Glu Lys Ala Gln Lys Ala Val Asn Ala Leu Phe
                        660                 665                 670
        Thr Ala Gly Arg Asn Ala Leu Gln Thr Asp Val Thr Asp Tyr Lys Val
                        675                 680                 685
        Asp Gln Val Ser Ile Leu Val Asp Cys Val Ser Gly Glu Leu Tyr Pro
        690                 695                 700
        Asn Glu Lys Arg Glu Leu Leu Ser Leu Val Lys Tyr Ala Lys Arg Leu
        705                 710                 715                 720
        Ser Tyr Ser Arg Asn Leu Leu Leu Asp Pro Thr Phe Asp Ser Ile Asn
                        725                 730                 735
```

```
Ser Ser Asp Glu Asn Gly Trp Tyr Gly Ser Asn Gly Ile Ala Ile Gly
        740                 745                 750

Asn Gly Asn Phe Val Phe Lys Gly Asn Tyr Leu Ile Phe Ser Gly Thr
        755                 760                 765

Asn Asp Thr Gln Tyr Pro Thr Tyr Leu Tyr Gln Lys Ile Asp Glu Ser
        770                 775                 780

Lys Leu Lys Glu Tyr Thr Arg Tyr Lys Leu Arg Gly Phe Ile Glu Asn
785                 790                 795                 800

Ser Gln Asp Leu Glu Ala Tyr Val Ile Arg Tyr Asp Ala Lys His Glu
                805                 810                 815

Thr Leu Asp Val Ser Asn Asn Leu Leu Pro Asp Ile Ser Pro Val Asn
        820                 825                 830

Ala Cys Gly Glu Pro Asn Arg Cys Ala Ala Leu Gln Tyr Leu Asp Glu
        835                 840                 845

Asn Pro Arg Leu Glu Cys Ser Ser Ile Gln Asp Gly Ile Leu Ser Asp
        850                 855                 860

Ser His Ser Phe Ser Leu Asn Ile Asp Thr Gly Ser Ile Asp Phe Asn
865                 870                 875                 880

Glu Asn Val Gly Ile Trp Val Leu Phe Lys Ile Ser Thr Pro Glu Gly
                885                 890                 895

Tyr Ala Lys Phe Gly Asn Leu Glu Val Ile Glu Asp Ser Pro Val Ile
        900                 905                 910

Gly Glu Ala Leu Ala Arg Val Lys Arg Gln Glu Thr Lys Trp Arg Asn
        915                 920                 925

Lys Leu Thr Gln Leu Arg Thr Glu Thr Gln Ala Ile Tyr Thr Arg Ala
930                 935                 940

Lys Gln Ala Ile Asp Asn Val Phe Thr Asn Ala Gln Asp Ser His Leu
945                 950                 955                 960

Lys Ile Gly Thr Thr Phe Ala Ala Ile Val Ala Ala Arg Lys Ile Val
                965                 970                 975

Gln Ser Ile Arg Glu Ala Tyr Met Ser Trp Leu Ser Ile Val Pro Gly
        980                 985                 990

Val Asn Tyr Pro Ile Phe Thr Glu Leu Asn Glu Arg Val Gln Arg Ala
        995                1000                1005

Phe Gln Leu Tyr Asp Val Arg Asn Val Val Arg Asn Gly Arg Phe
       1010                1015                1020

Leu Asn Gly Val Ser Asp Trp Ile Val Thr Ser Asp Val Lys Val
       1025                1030                1035

Gln Glu Glu Asn Gly Asn Asn Val Leu Val Leu Ser Asn Trp Asp
       1040                1045                1050

Ala Gln Val Leu Gln Cys Leu Lys Leu Tyr Gln Asp Arg Gly Tyr
       1055                1060                1065

Ile Leu Arg Val Thr Ala Arg Lys Glu Gly Leu Gly Glu Gly Tyr
       1070                1075                1080

Ile Thr Ile Thr Asp Glu Glu Gly His Thr Asp Gln Leu Thr Phe
       1085                1090                1095

Gly Thr Cys Glu Glu Ile Asp Ala Ser Asn Thr Phe Val Thr Thr
       1100                1105                1110

Gly Tyr Ile Thr Lys Glu Leu Glu Phe Phe Pro Asp Thr Glu Lys
       1115                1120                1125

Val Arg Ile Glu Ile Gly Glu Thr Glu Gly Thr Phe Gln Val Glu
       1130                1135                1140
```

-continued

```
Ser Ile  Glu Leu Phe Leu Met  Glu Asp Leu Cys
    1145                 1150

<210> SEQ ID NO 3
<211> LENGTH: 15
<212> TYPE: PRT
<213> ORGANISM: Bacillus thuringiensis
<220> FEATURE:
<223> OTHER INFORMATION: N-Terminal Peptide

<400> SEQUENCE: 3

Met Asp Ile Arg Asn Gln Asn Lys Tyr Glu Val Val Tyr Pro Ala
1               5                   10                  15

<210> SEQ ID NO 4
<211> LENGTH: 46
<212> TYPE: DNA
<213> ORGANISM: Artificial Sequence
<220> FEATURE:
<223> OTHER INFORMATION: Adapter Sequence
<400> SEQUENCE: 4
gctcgagtcg accgtggtac gcgtgtgtga gctcccggga tccggt                    46

<210> SEQ ID NO 5
<211> LENGTH: 28
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: h is a, c or t
<220> FEATURE:
<221> NAME/KEY: misc_feature
<222> LOCATION: (10)..(10)
<223> OTHER INFORMATION: m is a or c
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: r is a or g
<220> FEATURE:
<221> NAME/KEY: misc_feature
<222> LOCATION: (21)..(21)
<223> OTHER INFORMATION: y is c or t
<220> FEATURE:
<221> NAME/KEY: misc_feature
<222> LOCATION: (24)..(24)
<223> OTHER INFORMATION: r is a or g
<220> FEATURE:
<221> NAME/KEY: misc_feature
<222> LOCATION: (27)..(27)
<223> OTHER INFORMATION: y is c or t
<400> SEQUENCE: 5
atggatathm gnaatcaraa yaartayg                                        28

<210> SEQ ID NO 6
<211> LENGTH: 26
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: r is a or g
```

```
<220> FEATURE:
<221> NAME/KEY: misc_feature
<222> LOCATION: (15)..(15)
<223> OTHER INFORMATION: w is a or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: y is c or t
<220> FEATURE:
<221> NAME/KEY: misc_feature
<222> LOCATION: (24)..(24)
<223> OTHER INFORMATION: n is a, c, g, or t

<400> SEQUENCE: 6
aataaatatg argtwgtnta yccngc                                    26

<210> SEQ ID NO 7
<211> LENGTH: 19
<212> TYPE: DNA
<213> ORGANISM: Artificial Sequence
<220> FEATURE:
<223> OTHER INFORMATION: Synthetic primer

<400> SEQUENCE: 7
gctcgagtcg accgtggta                                            19

<210> SEQ ID NO 8
<211> LENGTH: 19
<212> TYPE: DNA
<213> ORGANISM: Artificial Sequence
<220> FEATURE:
<223> OTHER INFORMATION: Synthetic primer

<400> SEQUENCE: 8
gtacgcgtgt gtgagctcc                                            19

<210> SEQ ID NO 9
<211> LENGTH: 28
<212> TYPE: DNA
<213> ORGANISM: Artificial Sequence
<220> FEATURE:
<223> OTHER INFORMATION: Synthetic primer

<400> SEQUENCE: 9
ttctaataca acatcaaagt atccactc                                  28

<210> SEQ ID NO 10
<211> LENGTH: 27
<212> TYPE: DNA
<213> ORGANISM: Artificial Sequence
<220> FEATURE:
<223> OTHER INFORMATION: Synthetic primer

<400> SEQUENCE: 10
ggtatcgttc caatactaat tctaaac                                   27
```